(12) United States Patent
Guan et al.

(10) Patent No.: US 8,463,371 B2
(45) Date of Patent: Jun. 11, 2013

(54) SYSTEM AND METHOD FOR PROCESSING BRAIN SIGNALS IN A BCI SYSTEM

(75) Inventors: Cuntai Guan, Singapore (SG); Haihong Zhang, Singapore (SG); Chu Chuan Wang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 678 days.

(21) Appl. No.: 12/527,050

(22) PCT Filed: Feb. 11, 2008

(86) PCT No.: PCT/SG2008/000048
§ 371 (c)(1),
(2), (4) Date: Feb. 25, 2010

(87) PCT Pub. No.: WO2008/097201
PCT Pub. Date: Aug. 14, 2008

(65) Prior Publication Data
US 2010/0145214 A1     Jun. 10, 2010

Related U.S. Application Data

(60) Provisional application No. 60/900,322, filed on Feb. 9, 2007.

(51) Int. Cl.
*A61B 5/04*     (2006.01)

(52) U.S. Cl.
USPC ............................. 600/544; 600/545; 600/558

(58) Field of Classification Search
USPC ......................................... 600/544, 545, 558
See application file for complete search history.

(56) References Cited

U.S. PATENT DOCUMENTS

| 2003/0073921 | A1* | 4/2003 | Sohmer et al. | 600/544 |
| 2003/0176806 | A1* | 9/2003 | Pineda et al. | 600/544 |
| 2005/0017870 | A1* | 1/2005 | Allison et al. | 340/825.19 |
| 2005/0085744 | A1* | 4/2005 | Beverina et al. | 600/558 |
| 2005/0131311 | A1* | 6/2005 | Leuthardt et al. | 600/545 |
| 2007/0049844 | A1* | 3/2007 | Rosenfeld | 600/544 |

FOREIGN PATENT DOCUMENTS

WO     WO 03/073175 A2     9/2003

OTHER PUBLICATIONS

Mason, Steven et al. "Evaluating the Performance of Self-Paced Brain-Computer Interface Technology." Revision: 1.0 (draft), May 19, 2006. Entire document. See url: http://www.bci-info.tugraz.at/Research_Info/documents/articles/self_paced_tech_report-2006-05-19.pdf.

Mason, Steven et al., "A brain-controlled switch for asynchronous control applications." IEEE Transactions on Biomedical Engineering, vol. 47, No. 10, Oct. 2000, pp. 1297-1307. Entire document. See url: http://ieeexplore.ieee.org/ie15/10/18878/00871402.pdf?isNumber=.

(Continued)

*Primary Examiner* — Patricia Mallari
*Assistant Examiner* — Puya Agahi
(74) *Attorney, Agent, or Firm* — Volpe and Koenig, P.C.

(57) ABSTRACT

A system and method for processing brain signals in a BCI system. The method of processing brain signals in a BCI system includes the steps of processing the brain signals for control state detection to determine if a subject intends to use the BCI system; and processing the brain signals for command recognition if the control state detection method determines that the subject intends to use the BCI system.

10 Claims, 13 Drawing Sheets

OTHER PUBLICATIONS

Wolpaw, Jonathan et al., "Brain-computer interfaces for communication and control." Clinical Neurophysiology, Vo. 113, No. 6, pp. 767-791, 2002. Entire document. See url: http://www/infm/ulst.ac.uk.~girijesh/UGProjects/wolpaw.pdf.

Zhang, H. et al., "A Statistical Model of Brain Signals with Application to Brain-Computer Interface," 27th Int'l Conf. of the IEEE Engineering in Medicine and Biology Society (EMBS), Sep. 1-4, 2005, Shanghai, China, pp. 5388-5391. See url: http://ieeexplore.ieee.org/iel5/10755/33900/01615700.pdf.

Guan C. et al., "High performance P300 speller for brain-computer interface," IEEE Int'l Workshop on Biomedical Circuits and Systems, Dec. 1-3, 2004, pp. S3/5/INV-S3/13-16. Entire document. See url: http://ieeexplore.ieee.org/application/enterprise/entfilecabinetfull.jsp?ResultStart=0.

Sellers, E., "A P300-Based Brain-Computer Interface: Testing an Alternative Method of Communication," Nov. 17, 2004. Entire document. See url: http://etd.fcla.edu/SF/SFE0000536/Sellers_Diss_P300BCI.pdf.

Mason, Steven et al., "Evaluating the Performance of Self-Paced Brain-Computer Interface Technology", Revision 1.0 (draft), May 19, 2006.

Mason, Steven et al., "A Brain-Controlled Switch for Asynchronous Control Applications", IEEE Transactions on Biomedical Engineering, vol. 47, No. 10, Oct. 2000, pp. 1297-1307.

Wolpaw, Jonathan et al., "Brain-Computer Interfaces for Communication and Control", Clinical Neurophysiology 113 (2002) pp. 767-791.

Zhang, H. et al., "A Statistical Model of Brain Signals With Applications to Brain-computer Interface", 27th International Conference of the IEEE Engineering in Medicine and Biology Society (EMBS), Sep. 1-4, 2005, Shanghai, China, pp. 5388-5391.

Guan, C. et al., "High Performance P300 Speller for Brain-Computer Interface", IEEE International Workshop on Biomedical Circuits & Systems, Dec. 1-3, 2004, pp. S3.5.INV-S313/16.

Sellers, E. "A P300-Based Brain-Computer Interface: Testing an Alternative Method of Communication" Nov. 17, 2004.

Donchin, Emanual and Kevin M. Spencer, and Ranjith Wijesinghe, "The Mental Prosthesis: Assessing the Speed of a P300-Based Brain-Computer Interface", IEEE Transactions on Rehabilitation Engineering, vol. 8, No. 2, Jun. 2000, pp. 174-179.

Pfurtscheller, Gert and Christa Neuper, "Motor Imagery and Direct Brain-Computer Communication" IEEE vol. 89, No. 7, Jul. 2001, pp. 1123-1134.

Blankertz, Benjamin et al., "Boosting bit rates and error detection for the classification of fast-paces motor commands based on single-trial EEG analysis", IEEE Transactions on Neural Systems and Rehabilitation Engineering, vol. 11, No. 2, 2003, pp. 100-104.

Zhang, HaiHong, Asynchronous P300-based Brain-computer Interfaces: A Computational Approach with Statistical Models, IEEE, 2006, p. 1-10.

Lotte F., et al., "Topical Review; A review of classification algorithms for EEG-based brain-computer interfaces," Journal of Neural Engineering, Inst. of Physics Publ., Bristol, GB, vol. 4, No. 2, Jan. 31, 2007, pp. R1-13.

Olson B., et al., "Decoding High Level Signals for Asynchronous Brain Machine Interfaces," Engineering in Medicine and Biology Society, 2006. EMBS '06. 28th Ann. Int'l Conf. of the IEEE, Aug. 30, 2006, pp. 6569-6572.

Bashashati et al., "An improved asyhchronous brain interface: making use of the temporal history oft he LF-ASD feature vectors; an improved asynchronous brain interface," Journal of Neural Engineering, Inst. of Physics Publ., Bristol, GB, vol. 3, No. 2, Jun. 1, 2006, pp. 87-94.

EP08712873 Search Report, Mar. 25, 2010.

* cited by examiner

SYSTEM AND METHOD FOR PROCESSING BRAIN SIGNALS IN A BCI SYSTEM

FIELD OF INVENTION

The present invention relates broadly to a system and method for processing brain signals in a BCI system.

BACKGROUND

Brain Computer Interface (BCI) systems can provide an alternative way of communication and control for people with severe motor disabilities by allowing the human brain to control a computer directly without relying on normal neuromuscular pathways. The most important application for the BCI system is in the area of providing communication, control or rehabilitation tools for paralyzed people who are suffering from severe neuromuscular disorders so as to help compensate for or restore their lost abilities. For example, non-invasive, EEG-based BCI systems measure specific components of EEG activities, extract features from these components and translate these features into control signals to operate devices such as a cursor or a robot arm. Furthermore, BCI systems are also able to provide an important test-bed for the development of mathematical methods and multi-channel signal processing to derive command signals from brain activities.

A feature of brain signals that can be used in BCI systems is the evoke-related potential (ERP) for example, the P300 signal. The P300 signal is an endogenous, positive polarity component of the evoke-related potential (ERP) elicited in the brain in response to infrequent/oddball auditory, visual or somatosensory stimuli in a stream of frequent stimuli. It occurs at a latency of 300-600 ms after a target "oddball" stimulus and has a parietal distribution on the scalp. Furthermore, the amplitude of the P300 signal varies directly with the relevance of the eliciting events and inversely with the probability of the stimuli (or the inter-stimulus interval). On the other hand, exogenous factors such as stimulus size, stimulus duration and eccentricity do not usually give rise to significant changes in the P300 signal waveform. Coupled with the fact that almost all humans generate the P300 signal in response to infrequent/oddball stimuli, the stability of the P300 signal waveform in the presence of exogenous factors allows the P300 signal to be effectively used in BCI systems.

Traditional BCI systems, including P300-based BCI systems, work in a synchronous mode with the assumption that the user is always in the control state.

Therefore the BCI system is continuously translating concurrent brain signals to certain control commands even when the user does not intend to do so. This results in several false interpretations of the brain signals which in turn results in several responses of the BCI system not in accordance with the user's intent. Embodiments of the present invention seek to address one or more of the above problems.

SUMMARY

According to a first aspect of the present invention, there is provided a method of processing brain signals in a BCI system, the method comprising the steps of processing the brain signals for control state detection to determine if a subject intends to use the BCI system; and processing the brain signals for command recognition if the control state detection method determines that the subject intends to use the BCI system.

The step of processing the brain signals for control state detection may comprise providing a pre-defined set of stimuli; repeatedly activating the stimuli in rounds, wherein in each round each stimulus is activated once; detecting the respective brain signals in response to each of the stimuli being activated during each round; and determining whether over consecutive rounds the brain signal recorded for one of the stimuli corresponds to a P300 signal.

The determining whether over consecutive rounds the brain signal recorded for one of the stimuli corresponds to a P300 signal may be based on a fixed number of consecutive rounds.

The determining whether over consecutive rounds the brain signal recorded for one of the stimuli corresponds to a P300 signal may be based on a variable number of consecutive rounds.

After each round, different sets of consecutive rounds may be considered, with respective numbers of consecutive rounds in the different sets varying from a pre-defined minimum number to a current number of rounds.

The determining whether over consecutive rounds the brain signal recorded for one of the stimuli corresponds to a P300 signal may be based on the set of rounds with a highest posterior probability.

The determining whether over consecutive rounds the brain signal recorded for one of the stimuli corresponds to a P300 signal may be further based on a risk measure for evaluating a risk of making a wrong determination.

The risk measure may be based on a first posterior probability that for one of the stimuli the brain signal corresponds to a P300 signal in a current determination and a second posterior probability that, given a result of a previous determination, the brain signal of one of the stimuli corresponds to a P300 signal in the current determination.

The processing the brain signals for command recognition may comprise applying a classification method which determines a maximal averaged SVM score amongst the stimuli for having an associated brain signal corresponding to the P300 signal.

The stimuli may comprise one or more of a group consisting of a visual stimulus, an auditory or a somatosensory stimulus.

According to a second aspect of the present invention, there is provided a system for processing brain signals in a BCI system, the system comprising of a detection unit for processing the brain signals for control state detection to determine if a subject intends to use the BCI system; and a recognition unit for processing the brain signals for command recognition if the control state detection method determines that the subject intends to use the BCI system.

The system may further comprise a stimulation unit comprising a set of stimuli; wherein the stimulation unit repeatedly activates the stimuli in rounds, such that in each round each stimulus is activated once; and the detection unit detects the respective brain signals in response to each of the stimuli being activated during each round and determines whether over consecutive rounds the brain signal recorded for one of the stimuli corresponds to a P300 signal.

According to a third aspect of the present invention, there is provided a data storage medium having stored thereon computer code means for instructing a computer system to execute a method of classifying brain signals in a BCI system, the method comprising the steps of processing the brain signals for control state detection to determine if a subject intends to use the BCI system; and processing the brain signals for command recognition if the control state detection method determines that the subject intends to use the BCI system.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Figure 1:
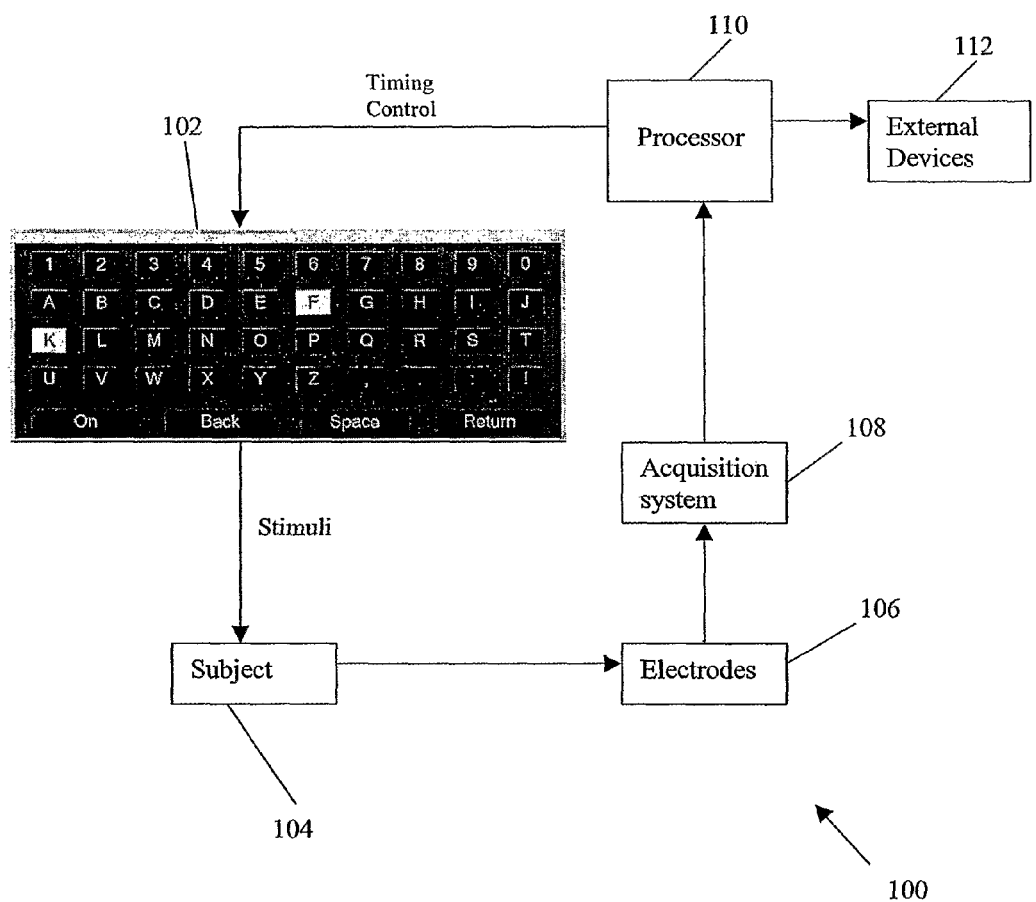
FIG. 1 illustrates a schematic block diagram of the BCI system according to an embodiment of the present invention.

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "calculating", "determining", "outputting", "transforming", "concatenating", "checking", "evaluating", "activating", "detecting" or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses an apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

An asynchronous BCI system is proposed to address the problems of traditional BCI systems mentioned above. The key difficulty in building an asynchronous BCI system is in developing a computational approach to distinguish between brain signals in the control state and those in the non-control state.

FIG. 1 illustrates a schematic block diagram of the BCI system 100 according to an embodiment of the present invention. In FIG. 1, a command panel 102 provides stimuli to a subject 104 and the subject 104 indicates his or her intentions by responding accordingly to the stimuli that the command panel 102 provides. The command panel 102 contains a set of buttons which would emit the stimuli in a random manner, with each button corresponding to a particular user command. The subject 104 is in turn connected to a set of electrodes 106. The set of electrodes 106 may be in the form of an EEG cap or may exist as individual Ag—AgCl electrodes connected to the surface of the subject's head. The set of electrodes 106 is then connected to an acquisition system 108 to acquire brain signals from the subject 104. The acquisition system 108 is in turn connected to a processor 110. The processor 110 carries out a processing scheme that would be further elaborated below. In addition, the processor 108 is also connected to the command panel 102 to control the timing of the stimuli emitted from the command panel 102. The processor 110 is in turn connected to external devices 112 such that output signals are sent from the processor 110 to the external devices 112. The external devices 112 then carry out the necessary actions in response to the output signals. The external devices 112 may be a cursor, a robot or an artificial limb.

An example embodiment of the present invention is described as follows. The command panel 102 contains a virtual keyboard with a few buttons representing characters and editing commands. When the BCI system 100 is in operation, the buttons of the command panel 102 flash randomly according to the timing control provided by the processor 110. When the subject 104 intends to use the BCI system 100 (control state), the subject 104 focuses on one of the buttons corresponding to the character or the editing command that the subject 104 intends to input. This leads to the appearance of evoke-related potentials such as P300 signals in the brain signals of the subject 104. When the subject 104 does not intend to use the BCI system 100 (non-control state), he or she does not focus on any button. Brain signals from the subject 104 are detected by the set of electrodes 106 and are acquired by the acquisition system 108. The brain signals are then sent to the processor 110 for processing using a processing scheme to be elaborated later. The processor 110 then transmits output signals to external devices 112, such as a computer screen which in turn displays the character corresponding to the button which the subject 104 is focusing on.

Figure 2:
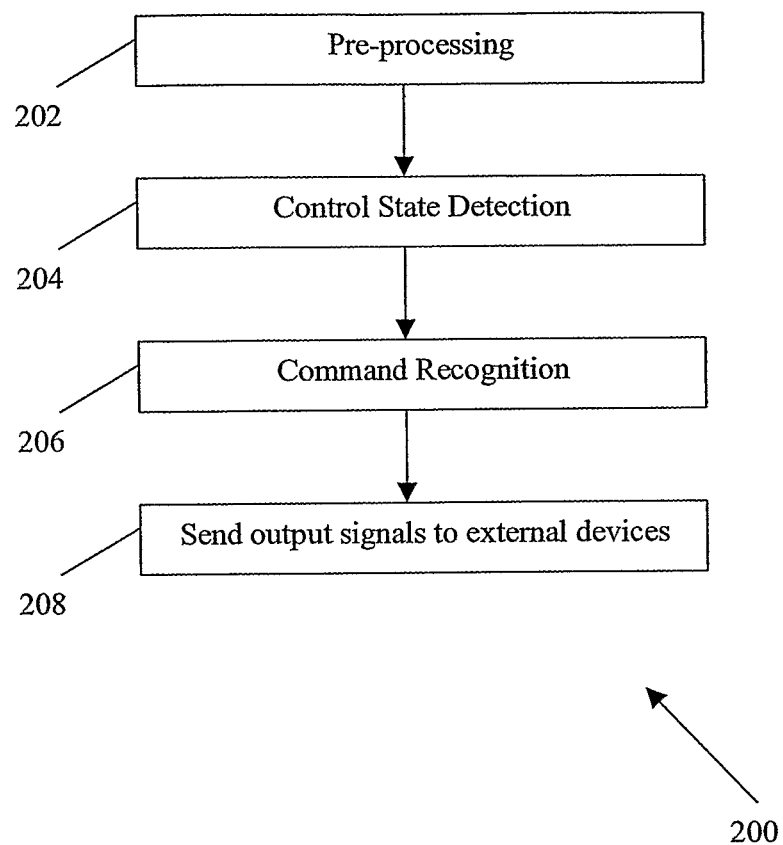
FIG. 2 shows a flow chart illustrating the processing scheme of the BCI system according to one embodiment of the present invention.

FIG. 2 shows a flow chart illustrating the processing scheme 200 of the BCI system according to one embodiment of the present invention. The processing scheme 200 first contains pre-processing step 202 whereby the acquired brain signals are transformed into a suitable form for further analysis. In one example, the pre-processing step 202 implements temporal filtering on the brain signals to remove high frequency noises and very slow waves with a $5^{th}$-order digital Butterworth filter with a passband of [0.5 Hz 15 Hz]. The filtered brain signals are then downsampled by a factor of 4 in order to reduce the computational complexity. The downsampled signals are then segmented from 100 ms to 500 ms after the onset of a stimulus from a button. In other examples, the pre-processing step 202 can include tasks such as detecting and removing artifacts in the acquired brain signals or re-referencing the brain signals.

Step 204 of the processing scheme 200 implements the control state detection in which a decision is made on whether or not the subject intends to use the BCI system. If it has been decided in step 204 that the user indeed intends to use the BCI system, step 206 is implemented to determine the command that the user intends to input into the BCI system. This command is transmitted to external devices via output signals in step 208 so that the external devices would carry out the necessary actions according to the subject's intent.

Figure 3:
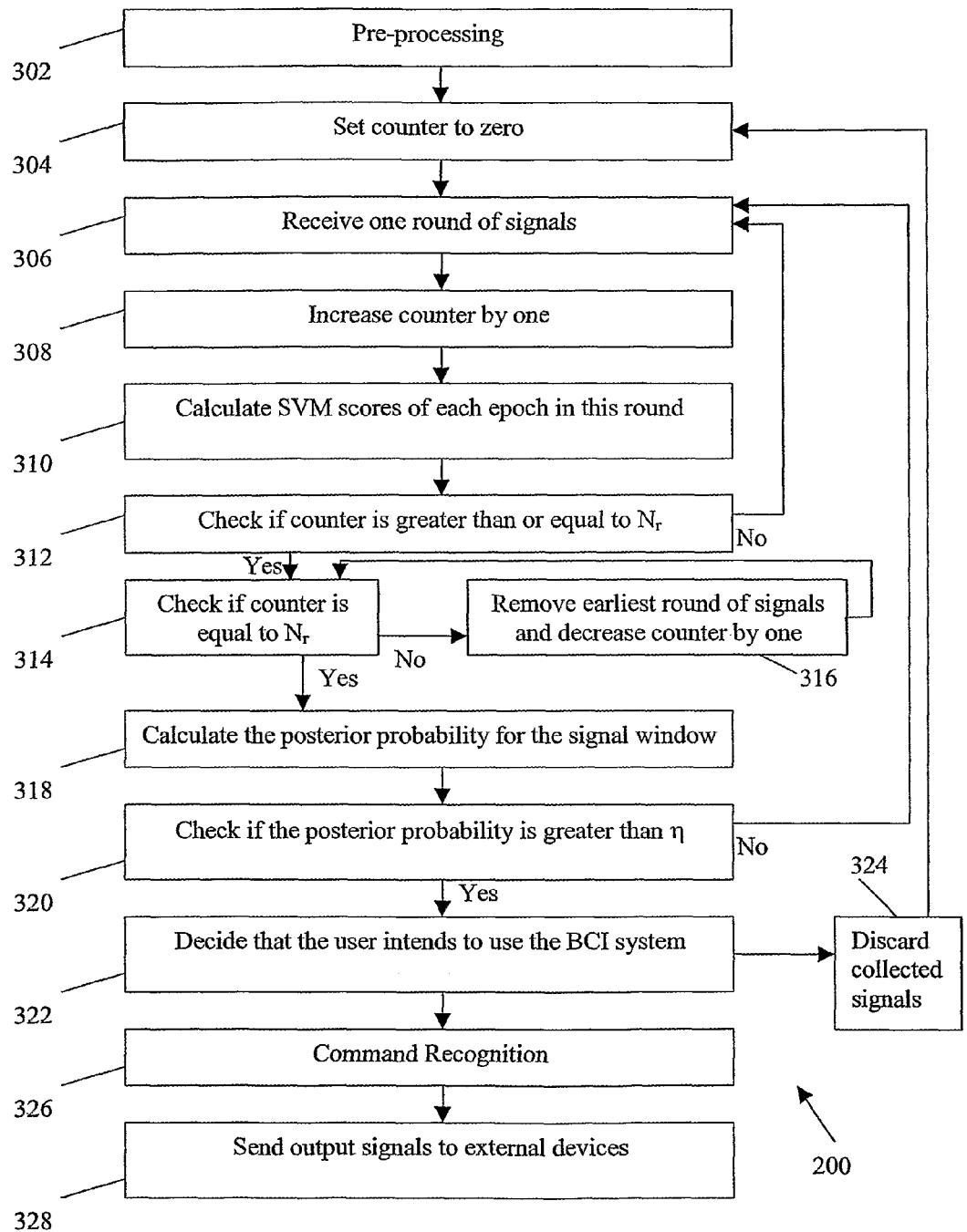
FIG. 3 shows a flowchart illustrating further details of the processing scheme according to a first example embodiment of the present invention.

FIG. 3 shows a flowchart illustrating further details of the processing scheme 200 according to a first example embodiment whereby a fixed length signal verification and a non risk-based decision making approach are used. In step 302, pre-processing is performed on the acquired brain signals so that the brain signals are transformed into a suitable form for further analysis and in step 304, a counter is created and set to zero.

In step 306, one round of brain signal epochs is received from the acquisition system. Each signal epoch is associated with a particular button on the command panel and denotes the signal segment from the subject's brain in response to a stimulus emitted from the button. In one example, the time segment from 150 ms to 500 ms after the onset of the stimulus from the button forms one signal epoch. One round of signal epochs is obtained after a complete cycle in which every button emits the stimulus once and only once. The counter is then increased by one in step 308.

In step 310, a Support Vector Machine (SVM) score is calculated for each signal epoch in the most recent round. The SVM score of each signal epoch is calculated according to Equation (1) whereby d is the SVM score and x is the feature vector constructed by concatenating the pre-processed signals obtained in step 302 and their dynamic features. The construction of x is shown in Equation (2) whereby s(1), . . . s(N) are the pre-processed signals and $\Delta s(1), \ldots, \Delta s(N)$ are the dynamic features. The construction of the dynamic feature $\Delta s(n)$ is in turn given by Equation (3) whereby $\alpha$ is a predefined normalization constant given by Equation (4) so that the dynamic features maintain similar variances as compared to the static features. In Equations (3) and (4), M is 5. Furthermore, $x_i$ is the $i^{th}$ support vector and k is a kernel function, for example a Gaussian function. In addition, parameters $a_i$ and b are predefined values set using prior training trials with labelled data. These parameters are set so as to achieve an accurate SVM model.

$$d = \sum_{i=1}^{N} a_i k(x, x_i) + b \tag{1}$$

$$x = [s(1)^T, \ldots, s(N)^T, \Delta s(1)^T, \ldots, \Delta s(N)^T]^T \tag{2}$$

$$\Delta s(n) \approx \alpha \sum_{m=-M}^{M} ms(n+m) \tag{3}$$

$$\alpha = \sum_{m=M}^{M} m^2 \tag{4}$$

In step 312, a check is performed to determine if the counter is greater than $N_r$, whereby $N_r(N_r \geq 3)$ is a predefined value that indicates the fixed number of signal rounds to be received before making a decision on whether the subject intends to use the BCI system. If the counter is not greater than or equal to $N_r$, steps 306 to 312 are repeated. Otherwise, step 314 is performed. Step 314 implements a check to determine if the counter is equal to $N_r$. If not, step 316 is performed whereby the earliest round of signals collected is discarded and the counter is decreased by one. Otherwise, step 318 is performed.

In step 318, a posterior probability $P_1$ is calculated for the signal window formed at the end of step 314.

A signal window, S, is a matrix containing at least $L_m$, ($L_m \geq 3$) rounds of signal epochs. An example of a signal window S with $N_r$ rounds of signal epochs is shown in Equation (5) whereby $s_i^{(j)}$ represents the signal epoch acquired in round j in response to a stimulus emitted by the $i^{th}$ button. In this example, there are a total of $N_s$ buttons in the command panel.

$$S = \begin{bmatrix} s_1^{(1)} & s_1^{(2)} & \cdots & s_1^{(N_r)} \\ s_2^{(1)} & s_2^{(2)} & \cdots & s_2^{(N_r)} \\ \vdots & \vdots & \ddots & \vdots \\ s_{N_s}^{(1)} & s_{N_s}^{(2)} & \cdots & s_{N_s}^{(N_r)} \end{bmatrix} \quad (5)$$

There are three types of signal epochs, denoted by $\Theta$, $\phi$ and $\bigcirc$ that each signal epoch, $s_j^{(i)}$, can be. These are the target epoch $\Theta$ which is associated with the event that the button targeted by the subject is emitting the stimulus, the non-target epoch $\phi$ which is associated with the event that the non-targeted buttons are emitting the stimuli and the non-control epoch $\bigcirc$ which represents an epoch when the subject is in the non-control state.

In one example, when the subject intends to use the BCI system, he or she would focus on one of the buttons on the command panel, the targeted button indicating the command that he or she wishes to input. When the button emits a stimulus, an evoke-related potential i.e. the target epoch ($\Theta$) would be recorded if the subject is focusing on this button. Otherwise, the $\phi$ signal would be recorded, $\phi$ representing the response of the brain to stimuli not receiving attention i.e. the non-target epoch. Hence, if the subject intends to use the BCI system, a single row of the signal window S in Equation (5) would show only the signal $\Theta$. Such a signal window is termed the control pattern $\Xi$ and an example of $\Xi$ is shown in Equation (6). On the other hand, if the subject does not intend to use the BCI system, a non-control pattern, $\Psi$, is obtained whereby an example of $\Psi$ is shown in Equation (7) with all rows having the non-control epoch $\bigcirc$.

$$\Xi = \begin{bmatrix} \Phi & \Phi & \cdots & \Phi \\ \vdots & \vdots & \ddots & \Phi \\ \Phi & \Phi & \cdots & \Phi \\ \Theta & \Theta & \Theta & \Theta \\ \Phi & \Phi & \cdots & \Phi \\ \vdots & \vdots & \ddots & \vdots \\ \Phi & \Phi & \Phi & \Phi \end{bmatrix} \quad (6)$$

$$\Psi = \begin{bmatrix} O & O & O & O \\ O & O & O & O \\ \vdots & \vdots & \vdots & \vdots \\ O & O & O & O \end{bmatrix} \quad (7)$$

The posterior probability $P_1$ calculated in step 318 refers to the posterior probability that the control pattern was received given the ensemble of SVM scores, D, in the signal window received. $P_1 = P(\Xi|D)$ is calculated according to Equation (8)

$$P_1 = P(\Xi \mid D) = \frac{\sum_{i=1}^{N_s} p(D \mid \Xi, R_i) P(\Xi, R_i)}{\sum_{j=1}^{N_s} p(D \mid \Xi, R_j) P(\Xi, R_j) + p(D \mid \Psi) P(\Psi)} \quad (8)$$

In Equation (8), $P(\Xi|R_i)$ is the probability that the control pattern was received, given that the single row of $\Theta$ signals lie in row $R_i$ and is given by Equation (9) whereby $P(\Xi) = P(\Psi) = 0.5$ assuming a 0.5 probability that the subject intends to use the BCI system.

$$P(\Xi, R_i) = \frac{1}{N_s} P(\Xi) \quad (9)$$

In addition, $p(D|\Xi,R_i)$ is the conditional probability that the SVM scores D are obtained given that the subject is attending to the $R_i$ button and is given by Equation (10) assuming that the signal epochs are independent.

$$p(D \mid \Xi, R_i) = \prod_j p(d_{ij} \mid \Theta) \prod_{k, j, k \neq i} p(d_{kj} \mid \Phi) \quad (10)$$

Similarly, $p(D|\Psi)$ is the conditional probability that the SVM scores D are obtained given that the subject is not attending to any button i.e. not intending to use the BCI system and is given by Equation (11).

$$P(D \mid \Psi) = \prod_{ij} p(d_{ij} \mid O) \quad (11)$$

In Equations (10) and (11), $p(d_{ij}|\Theta)$, $p(d_{ij}|\phi)$, $p(d_{ij}|\bigcirc)$ are the conditional probabilities that the SVM score $d_{ij}$ is obtained for the $i^{th}$ epoch in the $j^{th}$ round i.e. for $s_i^{(j)}$ in Equation (5) given that the signal epoch received is a target epoch, a non-target epoch or a non-control epoch respectively. The posterior probability for each epoch type can be modelled by Gaussian functions as shown in Equations (12), (13) and (14) for the target epoch, the non-target epoch and the non-control epoch respectively. In Equations (12), (13) and (14), $\mu$ represents the mean of the Gaussian distribution and $\sigma$ represents the standard deviation of the Gaussian distribution. These parameters can be obtained via a learning process from training samples using the conventional maximum a posteriori (MAP) method.

$$p(d|\Theta) = N(d - \mu_\Theta, \sigma_\Theta^2) \quad (12)$$

$$p(d|\phi) = N(d - \mu_\phi, \sigma_\phi^2) \quad (13)$$

$$p(d|\bigcirc) = N(d - \mu_o, \sigma_o^2) \quad (14)$$

After the calculation of the posterior probability $P_1$ in step 318, a check is performed in step 320 to determine if $P_1$ is greater than a pre-defined threshold $\eta$. The pre-defined threshold $\eta$ is determined according to the following steps in the example embodiment:

1) Training samples of control signals and simulating non-control signals are collected. The set of control signals are randomly partitioned into two subsets: set A and set B.
2) A SVM is trained to discriminate between all $\Theta$ and all $\phi$ signals in set A
3) The SVM is applied to set B and the outputs $d_{ij}$ are collected. The empirical mean and standard deviation of the outputs for $\Theta$ and $\phi$ signals are calculated and the sigmoid parameters for the posterior probabilities are obtained.
4) On set B, the posterior probability measure, $p_j^\Xi$ (probability that the control pattern is received given the ensemble of SVM scores, D) is calculated. Similarly, the measure $p_i^{(\Psi)}$ (probability that the non-control pattern is received given the ensemble of SVM scores, D) is obtained.

5) A threshold $\eta$ that produces the minimal false rejection rate, $\Theta_{ref}$, and false acceptance rate, $e_{apt}$, given by Equations (15) and (16) is obtained where $N_B$ is the number of control patterns in set B, $N_{NonC}$ is the number of non-control patterns for training and the u(x) is a unit-step function which takes the value of 0 if $x \geqq 0$ and takes the value of 1 otherwise.

$$e_{ref} = \frac{1}{N_B} \sum_i u(\eta - p_i^{(\Xi)}) \tag{15}$$

$$e_{apt} = \frac{1}{N_{NonC}} \sum_i u(p_i^{(\Psi)} - \eta) \tag{16}$$

If the posterior probability $P_1$ calculated in step 318 is greater than the threshold $\eta$, step 322 is performed in which a decision that the subject intends to use the BCI system is made. Otherwise, steps 306-320 are repeated. After the decision is made in step 322, steps 324 and 326 are performed. In step 324, all the collected signal rounds are discarded and the processing scheme restarts from step 304 in which the counter is set to zero.

In step 326, the process of command recognition is performed to determine the command that the subject intends to input into the BCI system. In one example, a classification method which picks up the maximal averaged SVM scores, d(i,t), among all the buttons is used. The button that the user has intended to select has the SVM score, c, given by Equation (17) whereby T is the detected signal time, i refers to the $i^{th}$ button. Details of Equation (17) are described in "T Manoj, C. Guan, and W. Jiankang. Robust classification of EEG signal for brain-computer interface. *IEEE Transactions on Neural Systems and Rehabilitation Engineering*, 14(1):24-29, 2006", the contents of which are incorporated herein by cross-reference.

$$c : \text{argmax}_i \sum_{t \in T} d(i, t) \tag{17}$$

Next, output signals based on the decided command in 326 are sent to external devices in step 328 so that the external devices can carry out the necessary actions according to the subject's intent.

Figure 4:
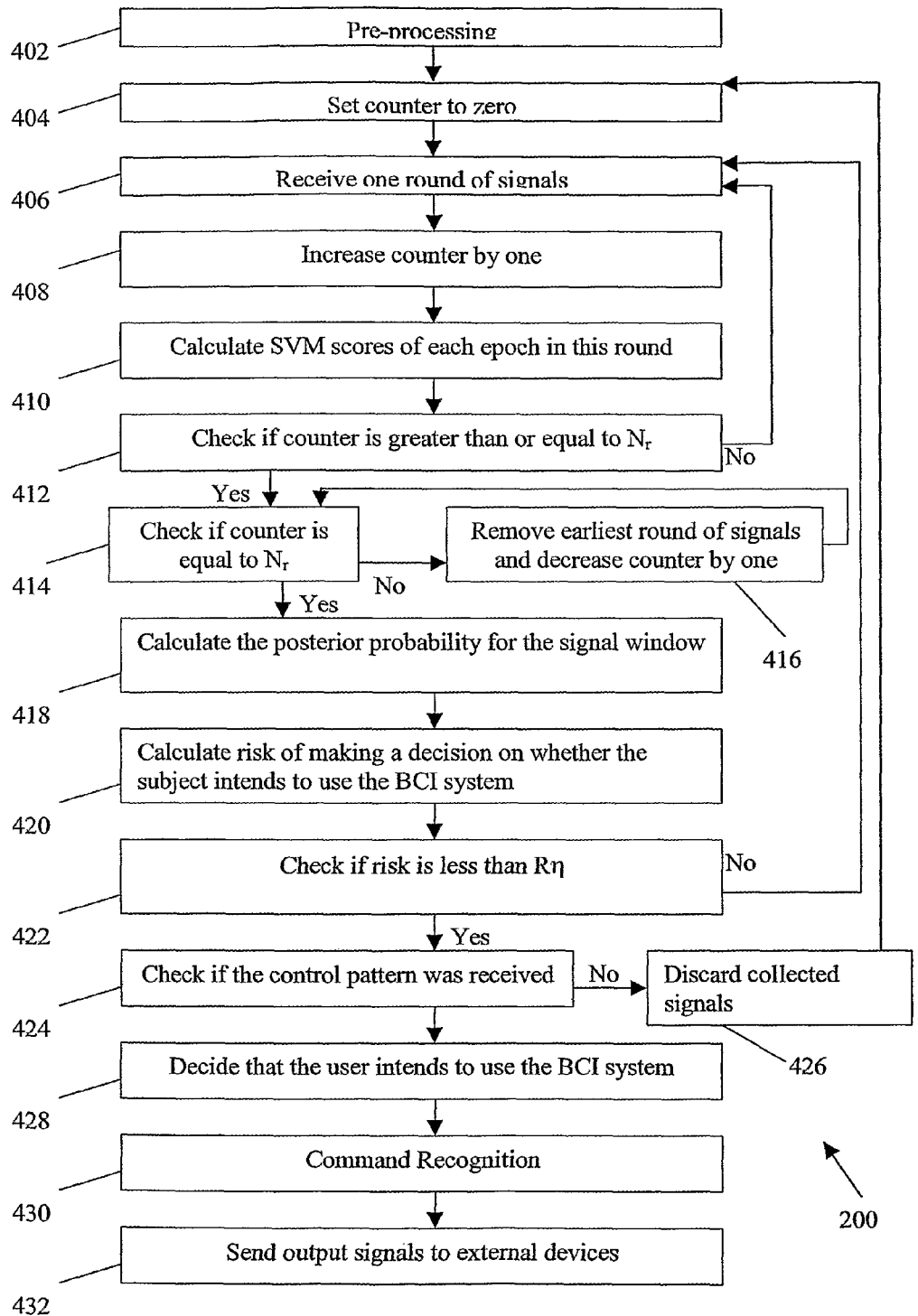
FIG. 4 shows a flowchart illustrating further details of the processing scheme according to a second example embodiment of the present invention.

FIG. 4 shows a flowchart illustrating further details of the processing scheme 200 according to a second example embodiment whereby a fixed length signal verification and a risk-based decision making approach are used. Steps 402-418 in FIG. 4 correspond to steps 302-318 in FIG. 3 and have been described above.

In step 420, a risk of making a decision on whether the subject intends to use the BCI system is calculated. Step 420 first calculates a posterior probability that the control signal is received given that the ensemble of SVM scores D is received and that the previous decision on whether the subject intends to use the BCI system is Y. Y may be the decision that the control pattern $\Xi$ was received or the decision that the non-control pattern $\Psi$ was received. This conditional probability is calculated according to Equation (18) whereby $P(\Xi|D)$ is the posterior probability calculated in step 418 and $P(\Xi|Y)$ is the posterior probability that the control signal is received given that the previous decision was Y. $P(\Xi|Y)$ is obtained by modelling the correlation between successive states using a simple Markov model.

$$P(\Xi|D,Y) = P(\Xi|Y)P(\Xi|D) \tag{18}$$

The risk of making a decision on whether the subject intends to use the BCI system is then calculated by Equation (19) in which $R_1$ is the risk of making a decision that the subject intends to use the BCI system and $R_2$ is the risk of making a decision that the subject does not intend to use the BCI system. The values of $R_1$ and $R_2$ are pre-defined using training samples.

$$R = R_1 P(\Xi|D,Y) + R_2 P(1 - P(\Xi|D,Y)) \tag{19}$$

In step 422, a check is performed to determine if the risk R obtained in step 420 is greater than a pre-defined threshold R$\eta$. R$\eta$ is the risk that would result in the minimum sum of false rejection rate and the false acceptance rate. R$\eta$ is determined using training data in the example embodiments. Two sets of data are collected during the training phase with one set used for model training and the other set used for evaluation. Based on the training data; the false rejection rate and the corresponding false acceptance rate for various thresholds are calculated. R$\eta$ corresponds to the threshold at which the sum of the false rejection error and the false acceptance error is minimal. If it has been decided in step 422 that the risk R is greater than R$\eta$, steps 406 to 422 are repeated. Otherwise, step 424 is performed.

In step 424, a check is performed to determine if the control pattern was received i.e. whether the subject intends to use the BCI system. Step 420 is performed by comparing $R_1 P(\Xi|D,Y)$ against $R_2(1 - P(\Xi|D,Y))$. If $R_1 P(\Xi|D,Y)$ is less than $R_2(1 - P(\Xi|D,Y))$, a decision that the control pattern was received is made and step 428 is performed. Otherwise, step 426 is performed whereby all the collected signal rounds are discarded and the processing scheme restarts from step 404 in which the counter is set to zero.

In step 428, a decision that the subject intends to use the BCI system is made and subsequently steps 430 and 432 are performed. Steps 430 and 432 correspond to steps 326 and 328 in FIG. 3 respectively and have been described earlier.

Figure 5:
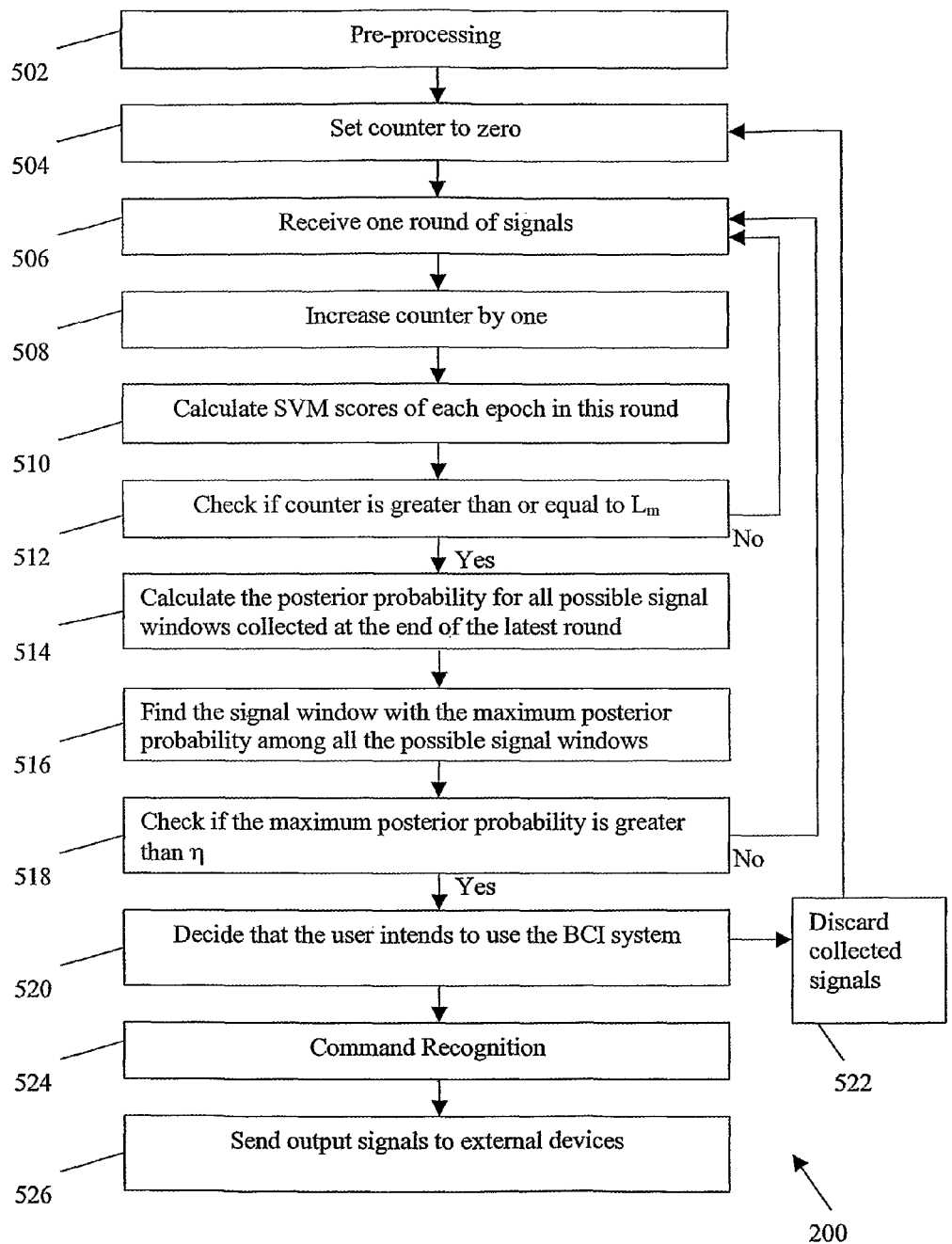
FIG. 5 shows a flowchart illustrating further details of the processing scheme according to a third example embodiment of the present invention.

FIG. 5 shows a flowchart illustrating further details of the processing scheme 200 according to a third example embodiment whereby a variable length signal verification and a non risk-based decision making approach are used. Steps 502-510 correspond to steps 302-310 in FIG. 3 and have been described above.

In step 512, a check is performed to determine if the counter is greater than $L_m$ ($L_m \geqq 3$) whereby $L_m$ indicates the minimum number of signal rounds to be received before making a decision on whether the subject intends to use the BCI system.

In step 514, the posterior probabilities for all the possible signal windows collected at the end of the most recent round are calculated. Each posterior probability is calculated according to Equation (8) above. Denoting the total number of rounds of signals collected by $k_r$, a possible signal window includes all signal rounds, from the most recently collected round to the round that was collected l rounds before the most recently collected round, whereby l is the length of the extracted signal window ($L_m \leqq l \leqq k_r$). For example, with $L_m = 3$ and $N_s$ buttons in the command panel, all the possible signal windows, $S_5$, $S_4$ and $S_3$, as illustrated in Equation (20) are extracted to give the full set of possible signal windows at the end of the $5^{th}$ round.

$$S_5 = \begin{bmatrix} s_1^{(1)} & s_1^{(2)} & s_1^{(3)} & s_1^{(4)} & s_1^{(5)} \\ s_2^{(1)} & s_2^{(2)} & s_2^{(3)} & s_2^{(4)} & s_2^{(5)} \\ \vdots & \vdots & \vdots & \vdots & \vdots \\ s_{N_s}^{(1)} & s_{N_s}^{(2)} & s_{N_s}^{(3)} & s_{N_s}^{(4)} & s_{N_s}^{(5)} \end{bmatrix} \quad (20)$$

$$S_4 = \begin{bmatrix} s_1^{(2)} & s_1^{(3)} & s_1^{(4)} & s_1^{(5)} \\ s_2^{(2)} & s_2^{(3)} & s_2^{(4)} & s_2^{(5)} \\ \vdots & \vdots & \vdots & \vdots \\ s_{N_s}^{(2)} & s_{N_s}^{(3)} & s_{N_s}^{(4)} & s_{N_s}^{(5)} \end{bmatrix}$$

$$S_3 = \begin{bmatrix} s_1^{(3)} & s_1^{(4)} & s_1^{(5)} \\ s_2^{(3)} & s_2^{(4)} & s_2^{(5)} \\ \vdots & \vdots & \vdots \\ s_{N_s}^{(3)} & s_{N_s}^{(4)} & s_{N_s}^{(5)} \end{bmatrix}$$

In step 516, the signal window with the maximum posterior probability among all the possible signal windows is found. The signal window, with length $l_m$, has a posterior probability, $P_{l_m}$, associated with it. In step 518, a check is performed to determine if $P_{l_m}$ is greater than a pre-defined threshold $\eta$ whereby $\eta$ is determined in the same way as in step 316 of FIG. 3 and has been described above. If $P_{l_m}$ is greater than $\eta$, step 520 is performed. Otherwise, steps 506-518 are repeated.

Steps 520-526 correspond to steps 322-328 in FIG. 3 respectively and have been described above.

Figure 6:
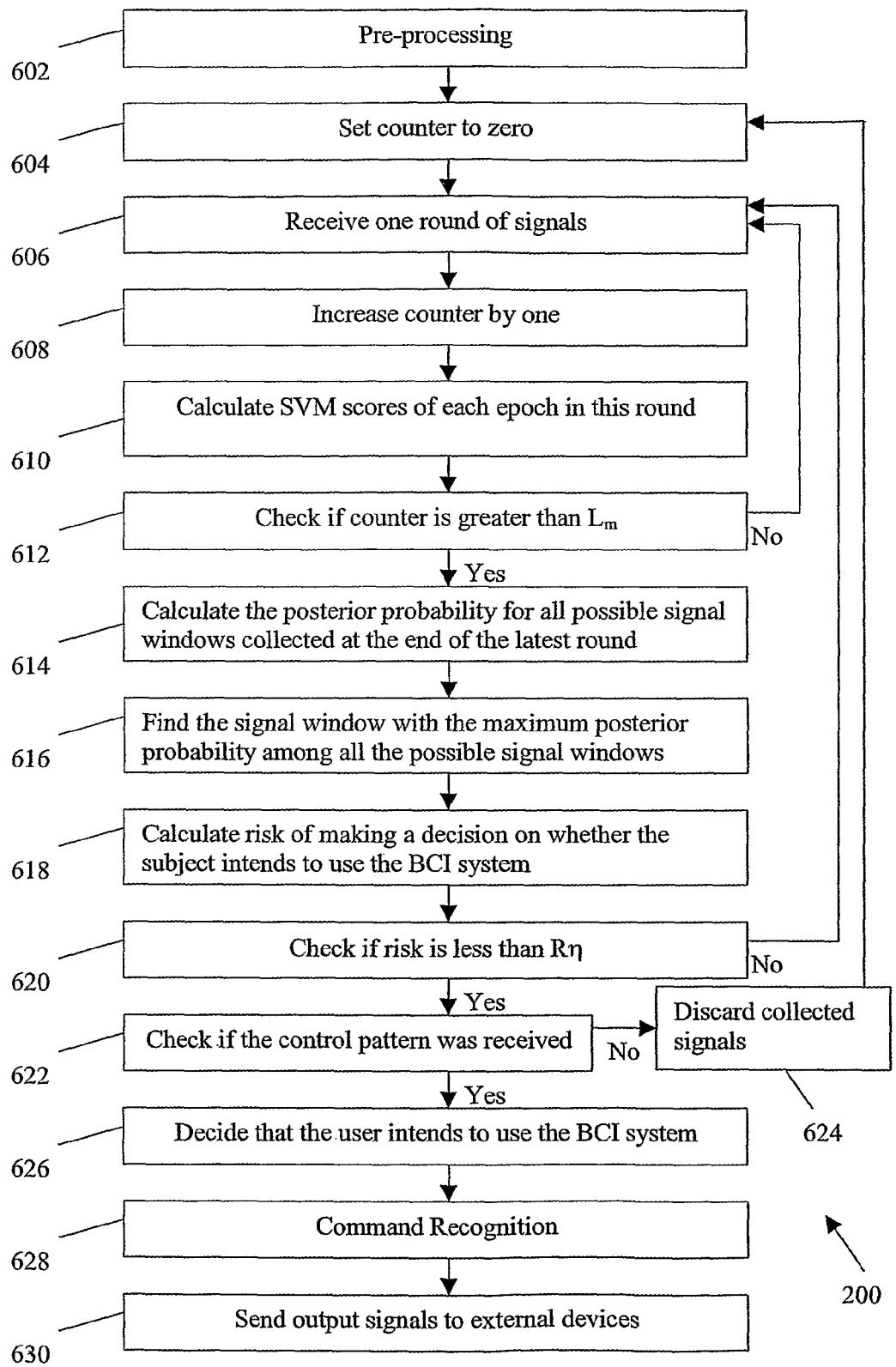
FIG. 6 shows a flowchart illustrating further details of the processing scheme according to a fourth example embodiment of the present invention.

FIG. 6 shows a flowchart illustrating further details of the processing scheme 200 according to a fourth example embodiment whereby a variable length signal verification and a risk-based decision making approach are used. In FIG. 6, steps 602-616 correspond to steps 502-516 of FIG. 5 and have been described above. In addition, steps 618-630 of FIG. 6 correspond to steps 420-432 in FIG. 4 and have also been described above.

The advantages conferred by the embodiments of the present invention can include:

Firstly, the BCI system in the embodiments of the present invention is an asynchronous BCI system which allows the subject to voluntarily switch between using and not using the BCI system without the aid of any other external inputs. This makes the BCI system more user-friendly especially for patients suffering from neurological disorders which result in them having short concentration spans such that they are unable to continuously attend to a single button for an extended period of time. The asynchronous BCI system is achieved mainly by using a rejection algorithm in the embodiments of the invention to remove undesired signals generated by the subject when he or she is not intending to use the BCI system or is not in a conscious or good control state. These undesired signals may lead to confusion and cause unwanted actions from the external devices. Thus, the BCI system with the rejection algorithm in the embodiments of the invention is more robust.

Secondly, since the attention level of a person may vary from time to time, having the variable length signal verification in the embodiments of the invention allows the BCI system to be more adaptive as it adapts to the attention level of the subject by finding the time window during which the attention level is perceived to be the highest: Furthermore, the variable length signal verification allows the BCI system to respond to the subject's command more promptly as the processing scheme automatically chooses the optimal length of the signal window at a time instead of waiting for, a fixed length of the signal window before further analysis is performed.

Thirdly, the risk-based decision making approach in the embodiments of the invention takes into account the history of the subject's intention, allowing the BCI system to be more accurate. For example, if a user of a BCI system has input a letter previously, he or she is more likely to continue to input another letter. The aim to minimize risk in this approach can also achieve a lower number of wrong decisions made.

To further illustrate the advantages of the embodiments of the present invention, experimental results from the implementation of the embodiments of the present invention are presented below.

Figure 7:
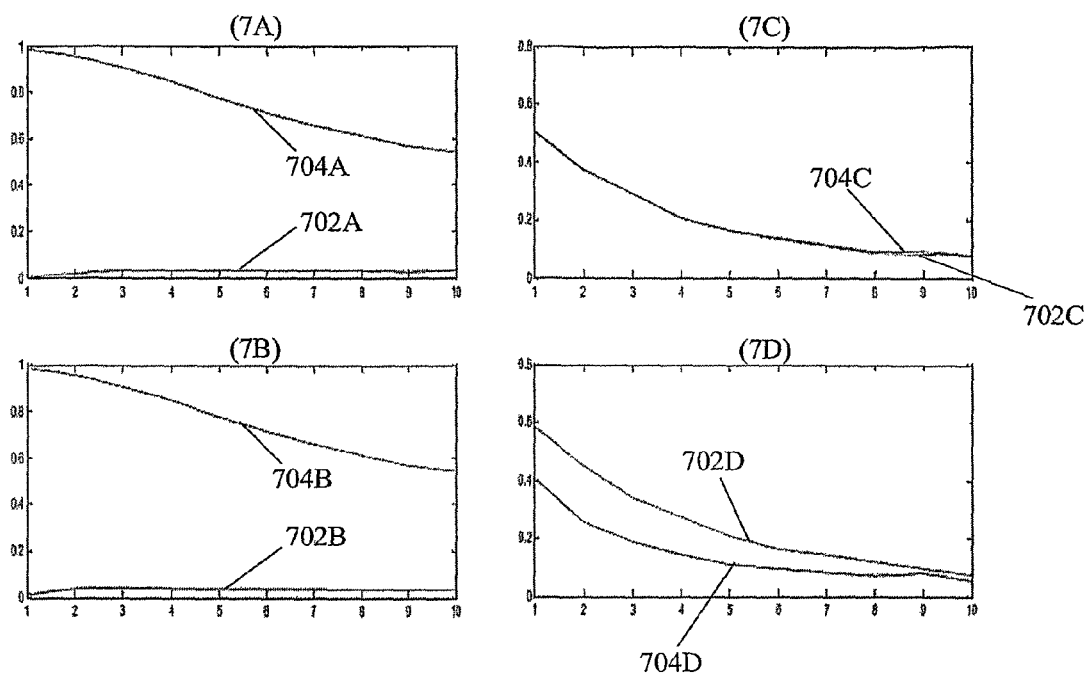
FIG. 7 shows subplots illustrating the experimental results from the implementation of the processing scheme according to the first example embodiment of the present invention.

FIG. 7 shows subplots illustrating the experimental results from the implementation of the processing scheme 200 according to the first example embodiment whereby a fixed length signal verification and a non risk-based decision making approach are used.

To obtain the results illustrated in FIG. 7, samples from six participants were collected. The sample set was divided equally into sets A and B, where set A was used for training the SVM and set B was used for producing statistics of the SVM scores. In the experiment, $N_r$ is equal to 10 i.e. 10 rounds of signals were collected before a decision on whether the subject intends to use the BCI system was made.

Since non-control patterns are so diversified, the focus in this experiment was on a special type of non-control pattern called the varying-focus pattern. Specifically, such patterns are generated if the subject changes focus from round to round. For example, a varying-focus pattern may have a $\Theta$ signal on $s_8^{(1)}$ for round 1, a $\Theta$ signal on $s_5^{(2)}$ for round 2 and so on, with the rest of the signals being the $\phi$ signal. The varying-focus patterns are closer to true control patterns because they contain $\Theta$ signals in each round. Therefore, it is more challenging and interesting to study the system performance for rejecting these patterns than for rejecting other patterns. Furthermore, such varying-focus patterns can be easily simulated. In the experiment, such patterns can be simulated by changing the position of the $\Theta$ signal across rounds.

In addition, a simple rejection method (baseline) was implemented in this experiment so as to highlight the advantage of the rejection method in the embodiments of the invention over the simple rejection method. Basically, this simple rejection method uses a gating mechanism and the threshold is set directly on SVM scores rather than on the probability measures. When an unknown pattern is received, the maximal SVM score is selected and tested against the threshold whereby the threshold corresponds to the cross-point of the SVM scores distributions for P/N-type patterns.

In FIG. 7, subplots 7A and 7B illustrate the false rejection rates (lines 702A and 702B) and the false acceptance rates (lines 704A and 704B). Subplots 7A and 7B illustrate the rates for the test sets and training sets respectively when the simple rejection algorithm is used. In addition, subplots 7C and 7D illustrate the false rejection rates (lines 702C and 702D) and false acceptance rates (lines 704C and 704D). Subplots 7C and 7D illustrate the rates for the test sets and the training sets respectively when the rejection algorithm according to the embodiments of the invention is used. It is clear from subplots 7A-D that the rejection algorithm according to the embodiments of the invention has achieved much lower false rejection rates than the simple rejection algorithm. More particular, taking the sum of the false acceptance rate and the false rejection rate as a measure of the performance of a rejection algorithm, subplots 7A-D illustrate that the embodiments of the invention have achieved a better performance as compared to the simple rejection algorithm since they have achieved a lower sum of the false acceptance rate and the false rejection rate.

Figure 8:
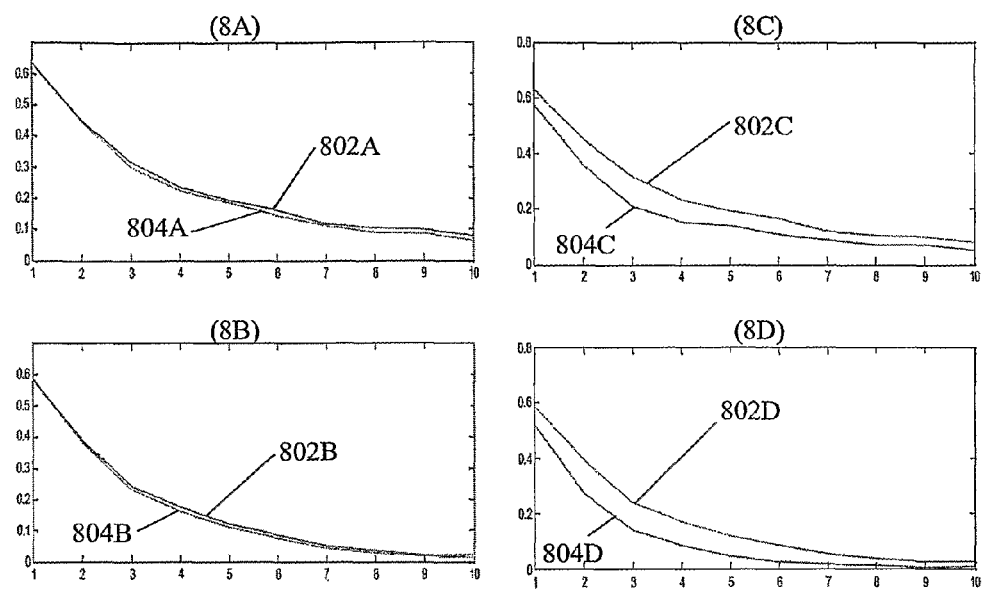
FIG. 8 shows subplots illustrating further experiment results from the implementation of the processing scheme according to the first example embodiment of the present invention.

FIG. 8 shows subplots illustrating further experiment results from the implementation of the processing scheme 200 according to the first example embodiment whereby a fixed length signal verification and a non risk-based decision making approach are used.

Subplots 8A and 8B show the recognition errors before (lines 802A, 802B) and after (lines 804A, 804B) rejection. Subplots 8A and 8B show the errors for the test and training data sets respectively when the simple rejection algorithm is used. Subplots 8C and 8D show the recognition errors before (lines 802C, 802D) and after. (lines 804C, 804D) rejection. Subplots 8C and 8D show the errors for the test and training data sets respectively when the rejection algorithm according to the embodiments of the invention is used. Clearly, the rejection algorithm according to the embodiments of the invention has achieved much lower recognition errors.

Tables 1 and 2 respectively show the recognition results obtained by the algorithm in the embodiments of the invention and by the simple rejection algorithm. Not only is it clear that lower recognition errors are achieved after rejection algorithms are applied, it is also apparent that the rejection algorithm according to the embodiments of the invention is more effective than the simple rejection algorithm as it achieves lower recognition errors.

TABLE 1

| Error rate | Before rejection | After rejection | Improvement |
|---|---|---|---|
| Training set | 7.9% | 5.1% | 35.4% |
| Test set | 2.4% | 0.9% | 62.5% |

TABLE 2

| Error rate | Before rejection | After rejection | Improvement |
|---|---|---|---|
| Training set | 7.9% | 6.6% | 16.5% |
| Test set | 2.4% | 1.7% | 29.2% |

Hence, the advantage of implementing the rejection algorithm in the embodiments of the invention for the implementation of an asynchronous BCI system is clearly illustrated in FIGS. 7 and 8, and Tables 1 and 2.

In another experiment implemented according to the third example of the invention whereby a variable length signal verification and a non risk-based decision making approach are used, the receiver operating characteristics (ROC) of the BCI system were analyzed. In this experiment, a few machine-guided tasks so as to conduct offline analysis using ROC curves were devised. These tasks were grouped into the following 3 sessions. Furthermore, the command panel in this experiment contained 9 buttons with the duration of one round being 900 ms.

The three sessions in which the tasks were grouped into are as follows. Session 1 consisted of 3 sections. In each of the first two sections, the subject attended to one button for 8 rounds, paused 2 seconds (as per the computer's video guide) and moved on to the next button until he or she had gone through all the 9 buttons. Hence, each of the two sections contained 72 rounds of signals, corresponding to 72 epochs of target P300 and 576 epochs of non-target P300 data. The two sections were both used to train the SVM to discriminate between target and non-target P300 data. In the $3^{rd}$ section, the monitor was closed and the subject stayed in the non-control state. Hence the data from the $3^{rd}$ section was used to estimate the distribution of SVM scores of non-control epochs.

In Session 2, the subject stayed in the control state and concentrated on one button for 50 rounds, paused 2 seconds (as per the computer's video guide), and moved on to the next button until he or she had gone through all the 9 buttons. The session was used to evaluate the proposed method in terms of the true positive rate (TPR).

Session 3 consisted of 3 sections. In each of the 3 sections, the subject stayed in the non-control state, paying no attention to any button or the computer display. Each section was as long as Session 2 which contained 50 rounds of signals. In the first section, the subject was singing a song. In the second section, the subject was relaxed with his or her eyes closed. In the third section, the subject was given a question sheet including a few arithmetic tasks, and was required to finish these tasks quickly. In total, the three sections allowed the evaluation of the embodiments of the invention in various non-control conditions. During the data analysis, the three sections were combined.

According to the timing scheme mentioned above, Sessions 1, 2 and 3 took approximately 4.5 minutes, 7 minutes and 21 minutes respectively. The subject was allowed to take a short break up to 2 minutes in between two sessions. The total, data collection on each subject ran for approximately 40 minutes, excluding the time taken for preparations.

In the experiment, a NuAmps device from Neuroscan, Inc. was used to measure the scalp brain signals. The brain signals were recorded from Ag—AgCl electrodes placed on the surface of each subject's head, corresponding to the inferior frontal, central and parietal regions of the brain. The digitizer device worked at a sampling rate of 250 Hz. Furthermore, to ensure an accurate recording of stimulus timing, a stimulus generation and data-acquisition software were used whereby a stimulus code representing a particular button flashing was sent to the hardware via the parallel port. Next, the signal machine inserted this stimulus code into a special channel. In this way, precise time information was recorded, even though there was a delay between a stimulus being generated and the corresponding brain signal being received. Throughout the experiment, an inter-stimulus interval at 100 ms was used Four healthy subjects, all male, between 20 to 45 years old participated in this experiment. To help the subjects concentrate on the task, they were asked to count the flashing of the target button.

The performance assessment of an asynchronous control system involves two factors: the capability for detecting the true events when the user is in the control state and the capability for rejecting the signals when the user is in the non-control state. For the first factor, the performance measure termed true positive rate (TPR) can be used. The TPR indicates the number of control events the system is able to detect within a time unit, for example, 1 minute. For the second factor, the measure termed false positive rate (FPR) can be used. The FPR indicates on average, the number of false events (in the non-control state) that the system will detect within a time unit.

Since a threshold on the posterior probability was used for the detection of the control state, both the TPR and the FPR are monotonical functions on the threshold value and when the threshold increases, both TPR and FPR will drop. Thus, there is always a trade-off between the TPR and the FPR when setting the threshold. The ROC curve can be used to indicate the performance of the BCI system whereby the ROC curve is a curve generated by plotting the TPR against the FPR.

Figure 9:
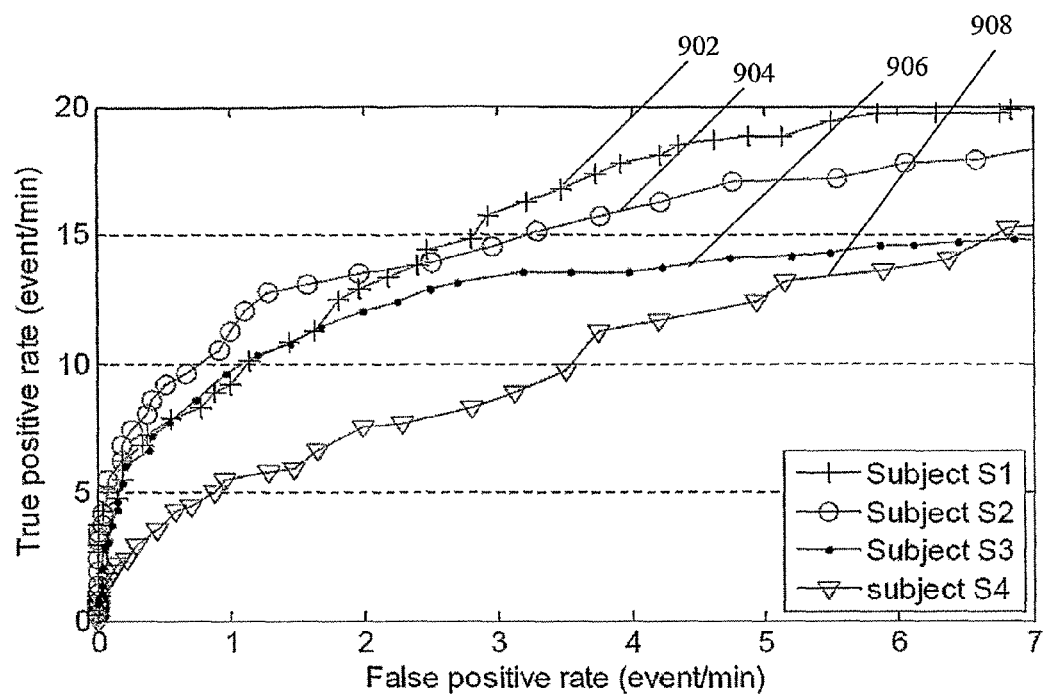
FIG. 9 shows a plot illustrating the ROC curves after the implementation of the processing scheme according to the third example embodiment of the present invention.

FIG. 9 shows a plot illustrating the ROC curves after the implementation of the processing scheme 200 according to the third example embodiment whereby a variable length signal verification and a non risk-based decision making approach are used. In FIG. 9, the ROC curves for each of the four subjects (lines 902, 904, 906 and 908) are shown Since a threshold was used on the posterior probability measure as obtained in Equation (8) for the detection of the control state, both the TPR and the FPR are monotonical functions on the threshold value. When the threshold increases, both the TPR and FPR will drop. Thus, there is always a trade-off between the TPR and the FPR when setting the threshold. The ROC curve can be used to indicate the performance of the detection system. In FIG. 9, each data point corresponds to a specific threshold and illustrates the tradeoff between the FPR and the TPR when different thresholds are chosen. For example, when a threshold is set such that the FPR is 1 event/minute for subject 908, the BCI system can achieve a TPR of approximately 5 events/minute for subject 908. However, if a threshold is set such that the FPR is 1 event/minute for subjects 902 or 906, the BCI system can achieve a TPR of approximately 10 events/minute for subjects 902 and 906. Similarly, if the threshold is set to achieve a TPR of 15 events/minute for subjects 902 and 904, the FPR would increase to approximately 3 events/minute for subjects 902 and 904, illustrating the cost or tradeoff between TPR and FPR.

To further evaluate the BCI system, the information transfer rate (ITR) of the BCI system is calculated. The ITR indicates the number of bits of information one is able to communicate effectively through the BCI and is given by Equation (21). In Equation (21), $n_r$ is the number of rounds per minute and P is the probability that the target is hit. (i.e. the control pattern is sent and the command is successfully recognized). P is determined by the false reject rate $F_{RR}$ and the recognition accuracy $F_a$ according to Equation (22).

$$B = n_r \{\log_2 N_s + P \log_2 P + (1-P) \log_2 [(1-P)/(N_s-1)]\} \quad (21)$$

$$P = (1 - F_{RR}) * F_a \quad (22)$$

Figure 10:
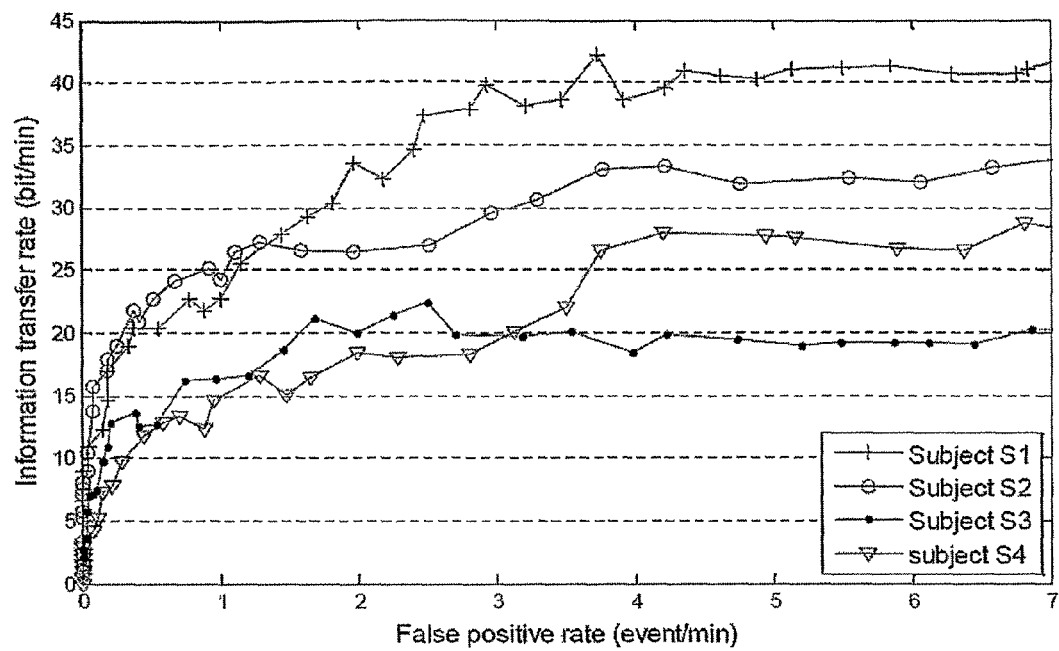
FIG. 10 shows a plot illustrating the relation between the ITR and the FPR after the implementation of the processing scheme according to the third example embodiment of the present invention.

FIG. 10 shows a plot illustrating the relation between the ITR and the FPR after the implementation of the processing scheme 200 according to the third example embodiment whereby a variable length signal verification and a non risk-based decision making approach are used. In FIG. 10, the ITR is generally monotonic over the FPR for each subject and the right limit of the FPR axis is 7 events per minute. The observation that each curve approaches an asymptote indicates that beyond FPR=3-4 events/minute, a subject-dependent ITR in the range from 20 bits/minute to 40 bits/minute can be achieved. With such a high ITR, the BCI system according to the third example of the invention has been shown to be one which can respond to the subject's command promptly.

In another experiment according to the third example embodiment whereby a variable length signal verification and a non risk-based decision making approach are used, the online performance of the BCI system was investigated. The BCI system was implemented in a real-time EEG processing system, using Visual C++ and C# and an online test protocol was designed.

The online test protocol consisted of the following. Four subjects were used in total. In an experiment session, a subject was seated comfortably in an armchair and had to continuously perform alternating control and non-control tasks. Two non-control tasks, reading and resting were included in this experiment. In the reading task, the subject would read some given stories aloud whereas in the resting task, the subject would take a rest with his or her eyes closed. One control task, inputting a given sequence of 32 digits, was performed. As the 9-button command panel was used, the digits from 1 to 8 were randomly selected to compose the sequence, while the digit '9' served as a "backspace" button to correct any input error during online testing.

Each session started with a reading task, followed by an input task, a rest task and an input task and ended with a reading task. The duration of each task was subject-dependent and no break was given in between consecutive tasks. Each subject spent 6 to 7 minutes in total on the reading task and 5 to 9 minutes on the resting task. Because the exact duration of each task was necessary to enable the accurate computation of the ITR and FPR, the actual start/end time points were recorded by having the subjects press a mouse button when they start or end each task. In addition, the threshold for the control-state detection is determined empirically for each subject using the training data so as to achieve an offline FPR lower than 1/minute. The BCI system in this experiment supplied online feedback to each subject by (a) highlighting detected digits quickly (0.5 seconds) in red; and (b) outputting the digits into a textbox on the computer monitor. After each session, the ITR was derived.

The results for this experiment are tabulated in Table 3. As shown in Table 3, the online performance of the BCI system according to the third example embodiment is such that on average, it can communicate at an ITR of 15 bits/minute in the control state, while producing 0.71 false positives per minute. Clearly, the BCI system according to the third example embodiment is able to respond to the subject promptly while keeping the number of false positives per minute low.

TABLE 3

|  | Subject 1 | Subject 2 | Subject 3 | Subject 4 | Average |
|---|---|---|---|---|---|
| ITR (bit/minute) | 21.67 | 17.37 | 10.60 | 10.37 | 15.0 |
| FPR (event/minute) | 0.20 | 0.71 | 0.39 | 1.54 | 0.71 |

In another experiment implemented according to the fourth example of the invention whereby a variable length signal verification and a risk-based decision making approach are used, data was collected and analyzed for an offline evaluation of five healthy subjects. A nine-button command, panel ($N_s$=9) was used in this experiment. Each subject spent two hours or so in the collection of three sessions of data These three sessions were as follows: Session 1 included 2 sets of 8 signal rounds when the subject was in the control state and the data collected was used to train P300/non-P300 classifiers (SVMs), Session 2 included 1 set of 50 signal rounds when the subject was in the control state and the data collected was used to evaluate the detection accuracy. Session 3 included 3 sets of 50 signal rounds when the subject was in the non-control state and the data was used to evaluate the false alarm (false acceptance) rate. In the first, second and third set, the subject was singing, resting with his or her eyes closed and calculating respectively.

Table 4 shows the ITR of the BCI system for each subject when the fixed length signal verification algorithm with $N_r$=4 (FL-4R) and $N_r$=8 (FL-8R) were used: Furthermore, Table 4 also shows the ITR of the BCI system for each subject when the variable length signal verification (VL) algorithm according to the fourth example embodiment was used. The results in Table 4 have been obtained with the false alarm rate at 0.05/second.

TABLE 4

|  | FL-4R | FL-8R | VL |
|---|---|---|---|
| Subject 1 | 35.71 | 31.16 | 45.17 |
| Subject 2 | 41.33 | 30.98 | 42.26 |
| Subject 3 | 9.87 | 17.13 | 14.81 |
| Subject 4 | 5.17 | 12.35 | 17.67 |
| Subject 5 | 12.57 | 14.29 | 17.67 |
| Average | 20.93 | 21.18 | 27.51 |

Clearly, the variable length signal verification (VL) algorithm improved the ITR by approximately 30% as compared to the fixed length signal verification methods. Hence, the advantage of having a variable length signal verification method in the embodiments of the present invention is clearly illustrated in Table 4, whereby the higher ITR of the BCI system implies that the BCI system can respond to the subject's command more promptly.

Figure 11:
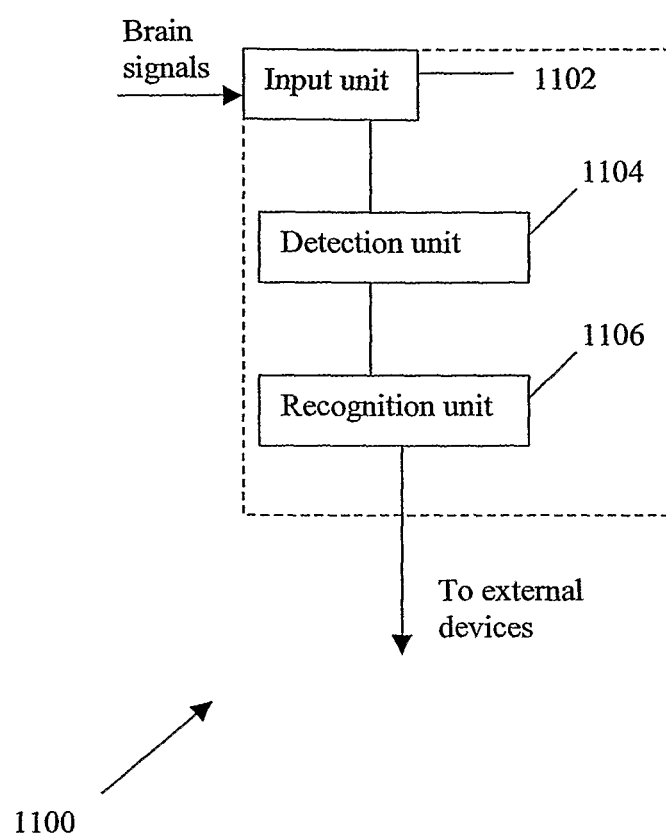
FIG. 11 illustrates a schematic block diagram of a system for processing brain signals in a BCI system according to one embodiment of the present invention.

FIG. 11 illustrates a schematic block diagram of a system 1100 for processing brain signals in a BCI system according to one embodiment of the present invention. The system 1100 includes an input unit 1102 to receive brain signals, a detection unit 1104 for processing the brain signals for control state detection to determine if the subject intends to use the BCI system and a recognition unit 1106 for a processing the brain signals for command recognition if the control state detection method determines that the subject intends to use the BCI system.

Figure 12:
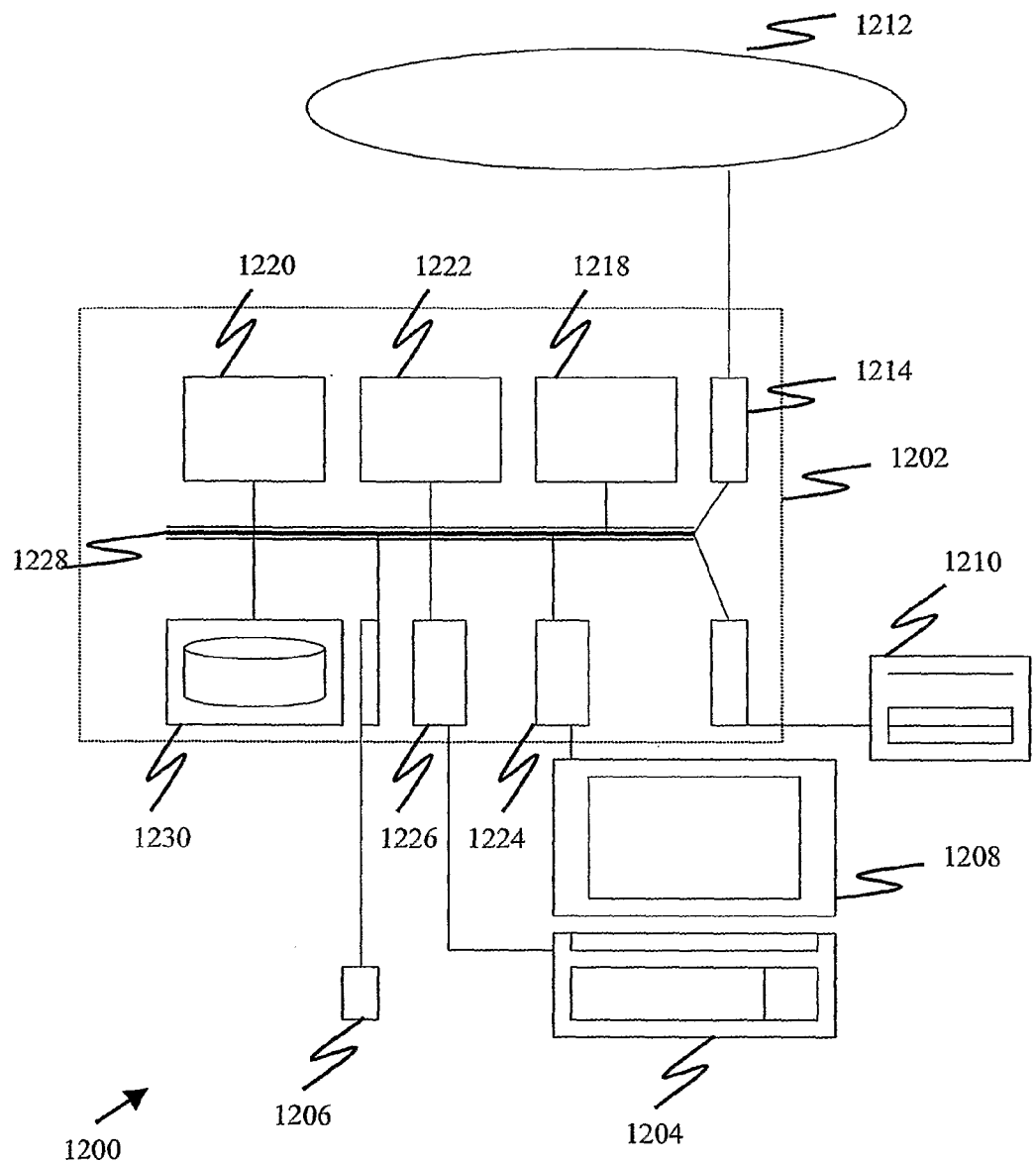
FIG. 12 illustrates a schematic block diagram of a system on which the method and system of the example embodiments can be implemented.

The method and system of the example embodiments can be implemented on a computer system 1200, schematically shown in FIG. 12. It may be implemented as software, such as a computer program being executed within the computer system 1200, and instructing the computer system 1200 to conduct the method of the example embodiment.

The computer system 1200 comprises a computer module 1202, input modules such as a keyboard 1204 and mouse 1206 and a plurality of output devices such as a display 1208, and printer 1210.

The computer module 1202 is connected to a computer network 1212 via a suitable transceiver device 1214, to enable access to e.g. the Internet or other network systems such as Local Area Network (LAN) or Wide Area Network (WAN).

The computer module 1202 in the example includes a processor 1218, a Random Access Memory (RAM) 1220 and a Read Only Memory (ROM) 1222. The computer module 1202 also includes a number of Input/Output (I/O) interfaces, for example I/O interface 1224 to the display 1208, and I/O interface 1226 to the keyboard 1204.

The components of the computer module 1202 typically communicate via an interconnected bus 1228 and in a manner known to the person skilled in the relevant art.

The application program is typically supplied to the user of the computer system 1200 encoded on a data storage medium such as a CD-ROM or flash memory carrier and read utilising a corresponding data storage medium drive of a data storage device 1230. The application program is read and controlled, in its execution by the processor 1218. Intermediate storage of program data may be accomplished using RAM 1220.

Figure 13:
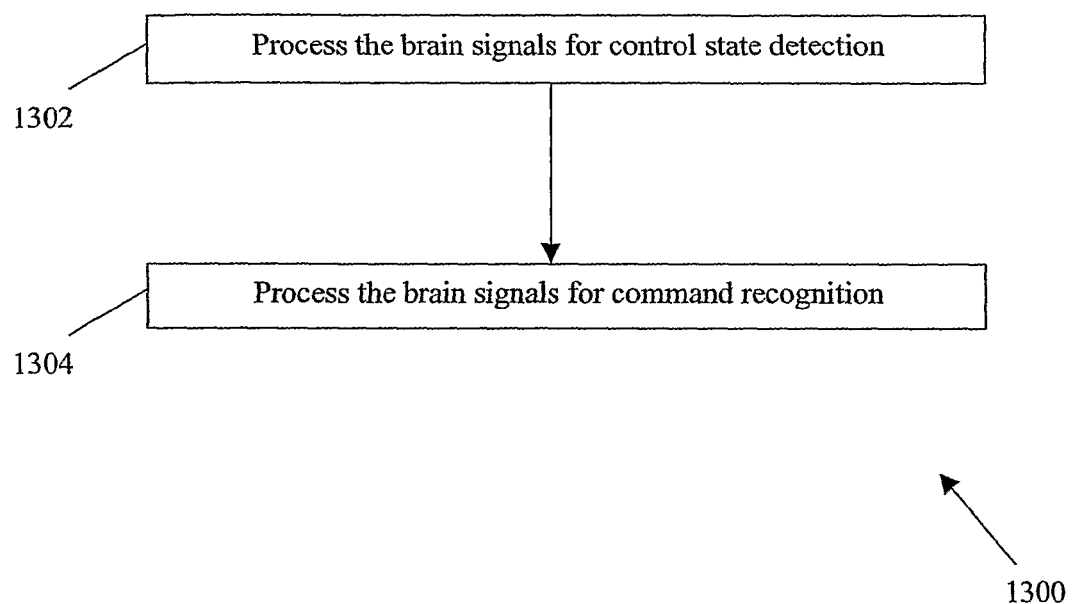
FIG. 13 shows a flowchart illustrating a method for processing brain signals in a BCI system according to one embodiment of the present invention.

FIG. 13 shows a flowchart illustrating a method 1300 for processing brain signals in a BCI system according to one embodiment of the present invention. In step 1302, brain signals are processed for control state detection to determine if the subject intends to use the BCI system. In step 1304, brain signals are processed for command recognition if the control state detection method determines that the subject intends to use the BCI system.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive. For example, while a command panel using visual stimuli has been described in the example embodiments of the present invention, command panels using other types of stimuli such as auditory or somatosensory stimuli can also be used in the embodiments of the present invention.

The invention claimed is:

1. A computer-implemented method of processing brain signals in a Brain Computer Interface (BCI) system, the method comprising the steps of:

providing a pre-defined set of stimuli and repeatedly activating the stimuli in rounds, wherein in each of the rounds each of the stimuli is activated once;

detecting the respective brain signals in response to each of the stimuli being activated during each of the rounds;

determining whether a subject intends to use the BCI system based on the detected respective brain signals using a processor; and processing the brain signals for command recognition if it is determined that the subject intends to use the BCI system;

wherein the determining whether the subject intends to use the BCI system comprises:

after k collected number of rounds, determining all the possible signal windows covering l consecutive rounds, from a most recently collected round to a round that was collected l rounds before the most recently collected round, where $L \leq l \leq k$, L is a predefined minimum value, and $3 \leq L \leq k$;

determining the signal window from among said possible signal windows which gives a highest posterior probability that a control pattern was received in said signal window; and checking whether said highest posterior probability is greater than a predefined first threshold.

2. The method as claimed in claim 1, wherein the determining whether the subject intends to use the BCI system further comprises collecting an additional round of the respective brain signals if the highest posterior probability is not greater than the first threshold.

3. The method as claimed in claim 1, wherein the determining whether the subject intends to use the BCI system further comprises calculating a risk of making a decision on whether the subject intends to use the BCI system based on the signal window which gives the highest posterior probability.

4. The method as claimed in claim 3, further comprising collecting an additional round of the respective brain signals if the risk is not lower than a second threshold.

5. The method as claimed in claim 1, wherein the processing the brain signals for command recognition is performed over said signal window which gives a highest posterior probability.

6. The method as claimed in claim 1, wherein the determining whether the subject intends to use the BCI system comprises determining whether for one of the stimuli the brain signal corresponds to a P300 signal.

7. The method as claimed in claim 6, wherein the processing the brain signals for the command recognition comprises applying a classification method which determines a maximal averaged Support Vector Machine (SVM) score amongst the stimuli for having an associated brain signal corresponding to the P300 signal.

8. The method as claimed in claim 1, wherein the stimuli comprise one or more of a group consisting of a visual stimulus, an auditory or a somatosensory stimulus.

9. A system for processing brain signals in a Brain Computer Interface (BCI) system, the system comprising of:
- a stimulation unit comprising a set of stimuli, wherein the stimulation unit repeatedly activates the stimuli in rounds, such that in each of the rounds each of the stimuli is activated once;
- a detection unit for detecting the respective brain signals in response to each of the stimuli being activated during each of the rounds and for determining whether a subject intends to use the BCI system based on the detected respective brain signals; and
- a recognition unit for processing the brain signals for command recognition if the detection unit determines that the subject intends to use the BCI system,
- wherein the detection unit, after k collected number of rounds, determines all the possible signal windows covering l consecutive rounds, from a most recently collected round to a round that was collected l rounds before the most recently collected round, where $L<l<k$, L is a predefined minimum value, and $3<L<k$;
- determines the signal window from among said possible signal windows which gives a highest posterior probability that a control pattern was received in said signal window; and checking whether said highest posterior probability is greater than a predefined first threshold.

10. A non-transitory data storage medium having stored thereon computer code means for instructing a computer system to execute a method of classifying brain signals in a Brain Computer Interface (BCI) system, the method comprising the steps of:
- providing a pre-defined set of stimuli and repeatedly activating the stimuli in rounds, wherein in each of the rounds each of the stimuli is activated once;
- detecting the respective brain signals in response to each of the stimuli being activated during each of the rounds;
- determining whether a subject intends to use the BCI system based on the detected respective brain signals; and
- processing the brain signals for command recognition if it is determined that the subject intends to use the BCI system;
- wherein the determining whether the subject intends to use the BCI system comprises:
- after k collected number of rounds, determining all the possible signal windows covering l consecutive rounds, from a most recently collected round to a round that was collected l rounds before the most recently collected round, where $L<l<k$, L is a predefined minimum value, and $3<L<k$;
- determining the signal window from among said possible signal windows which gives a highest posterior probability that a control pattern was received in said signal window; and
- checking whether said highest posterior probability is greater than a predefined first threshold.

* * * * *